(12) United States Patent
Roose et al.

(10) Patent No.: US 9,980,489 B2
(45) Date of Patent: May 29, 2018

(54) STABILIZED BIO-AVAILABLE SOLUBLE SILICATE SOLUTION

(75) Inventors: Peter Roose, Deurle (BE); Marc Demuynck, Wondelgem (BE); Johan De Saegher, Destelbergen (BE); Jean-Michel Rabasse, Paris (FR)

(73) Assignee: Taminco BVBA, Ghent (BE)

( * ) Notice: Subject to any disclaimer, the term of this patent is extended or adjusted under 35 U.S.C. 154(b) by 500 days.

(21) Appl. No.: 13/638,528

(22) PCT Filed: Mar. 24, 2011

(86) PCT No.: PCT/EP2011/054556
§ 371 (c)(1),
(2), (4) Date: Feb. 8, 2013

(87) PCT Pub. No.: WO2011/120872
PCT Pub. Date: Oct. 6, 2011

(65) Prior Publication Data
US 2013/0130902 A1  May 23, 2013

(30) Foreign Application Priority Data

Mar. 31, 2010  (EP) .................................... 10158686
May 6, 2010  (EP) .................................... 10162186

(51) Int. Cl.

| | |
|---|---|
| A01N 59/00 | (2006.01) |
| A01N 47/14 | (2006.01) |
| C05D 9/02 | (2006.01) |
| C05G 3/02 | (2006.01) |
| C05F 11/10 | (2006.01) |
| A01N 25/22 | (2006.01) |
| A01N 25/02 | (2006.01) |
| A01N 47/12 | (2006.01) |
| A01N 25/12 | (2006.01) |
| A23D 7/005 | (2006.01) |
| C01B 33/22 | (2006.01) |
| C05C 9/00 | (2006.01) |
| C05D 1/00 | (2006.01) |
| A61K 8/25 | (2006.01) |
| A61K 33/00 | (2006.01) |
| C05D 9/00 | (2006.01) |
| A23K 20/28 | (2016.01) |
| A61K 8/34 | (2006.01) |
| A61K 8/42 | (2006.01) |
| A61K 8/44 | (2006.01) |
| A61Q 19/00 | (2006.01) |

(52) U.S. Cl.
CPC ............ *A01N 59/00* (2013.01); *A01N 25/02* (2013.01); *A01N 25/12* (2013.01); *A01N 25/22* (2013.01); *A01N 47/12* (2013.01); *A01N 47/14* (2013.01); *A23D 7/0053* (2013.01); *A23K 20/28* (2016.05); *A61K 8/25* (2013.01); *A61K 8/345* (2013.01); *A61K 8/42* (2013.01); *A61K 8/44* (2013.01); *A61K 33/00* (2013.01); *A61Q 19/00* (2013.01); *C01B 33/22* (2013.01); *C05C 9/00* (2013.01); *C05D 1/00* (2013.01); *C05D 9/00* (2013.01); *C05D 9/02* (2013.01); *C05F 11/10* (2013.01); *C05G 3/02* (2013.01); *A61K 2800/10* (2013.01)

(58) Field of Classification Search
CPC ........ A01N 59/00; A01N 25/02; A01N 25/12; A01N 25/22; A01N 47/12; A01N 47/14; A01N 2300/00; C05D 9/00; C05D 1/00; C05D 9/02; A23K 1/1756; A23D 7/0053; A23L 1/304; C01B 33/22; C05C 9/00; A61K 33/00; A61K 8/25; C05F 11/10; C05G 3/02
USPC ....... 424/600, 722; 504/187; 426/648; 71/11
See application file for complete search history.

(56) References Cited

U.S. PATENT DOCUMENTS

| | | | | |
|---|---|---|---|---|
| 5,922,360 | A * | 7/1999 | Bronder | 424/600 |
| 6,673,375 | B2 * | 1/2004 | Choi et al. | 424/658 |
| 2003/0099676 | A1 * | 5/2003 | Van Den Berghe | 424/401 |
| 2004/0197270 | A1 * | 10/2004 | Mundschenk | A01N 25/06 424/45 |
| 2004/0220137 | A1 * | 11/2004 | Sauermann | A61K 8/06 514/54 |
| 2006/0165815 | A1 * | 7/2006 | Vanden Berghe | 424/687 |

FOREIGN PATENT DOCUMENTS

| | | |
|---|---|---|
| DE | 202009011154 U1 | 10/2009 |
| WO | WO 2009/127256 A1 | 10/2009 |
| WO | WO 2010/055166 A2 | 5/2010 |

OTHER PUBLICATIONS

Aguilar et al., "Choline-stabilised orthosilicic acid added for nutritional purposes to food supplements", The European Food Safety Authority Journal (2009) 948, 1-23.*
"Final Report on the Safety Assessment of Potassium Silicate, Sodium Metasilicate^ and Sodium Silicate", International Journal of Toxicolgy.24(Suppl. 1): 103-117, 2005.*

(Continued)

*Primary Examiner* — John Pak
*Assistant Examiner* — Nathan W Schlientz
(74) *Attorney, Agent, or Firm* — Robert C. Morriss

(57) ABSTRACT

The present invention relates to dissolved silicate compositions in which the dissolved silicate is stabilized by at least two selected osmolytes and is therefore bioavailable. The composition and its dilutions are stable over a long period of time and are used in a wide field of applications for the benefit of living organisms such as plants, animals and humans.

8 Claims, 3 Drawing Sheets

(56) References Cited

OTHER PUBLICATIONS

Epstein E.; "Silicon"; Annual Review of Plant Physiology and Plant Molecular Biology; 1999; 50; pp. 641-664.
Epstein E.; "Silicon: its manifold roles in plants"; Annals of Applied Biology, 155; (2009); pp. 155-160.
Reynolds O.L. et al; "Silicon-augmented resistance of plants to herbivorous insects: a review"; Annals of Applied Biology; 155; (2009); pp. 171-186.
Liang Y. et al.; "Mechanisms of silicon-mediated alleviation of abiotic stresses in higher plants: A review"; Environmental Pollution; 147; (2007); pp. 422-428.
Brunings A.M. et al.; "Differential gene expression of rice in response to silicon and rice blast fungus *Magnaporthe oryzae*"; Annals of Applied Biology; 155; (2009); pp. 161-170.
Robberecht H. et al.; "Dietary silicon intake in Belgium: Sources, availability from foods, and human serum levels"; Science of the Total Environment; 407; (2009); pp. 4777-4782.
Sripanyakorn S. et al.; "The comparative absorption of silicon from different foods and food supplements"; British Journal of Nutrition; (2009); 102; pp. 825-834.
International Search Report with Date of Mailing Jan. 30, 2012 for International Application No. PCT/EP2011/054556.
Notice of Opposition dated Aug. 31, 2015 received for European Patent No. 2 371 220.
Reply to Notice of Opposition dated Apr. 22, 2016 for European Patent No. 2 371 220.
Summons to Attend Oral Proceedings Pursuant to Rule 115(1) EPC dated Jul. 8, 2016 for European Patent Application No. 10162186.0—1454/2371220.
Preliminary Opinion of the Opposition Division dated Jul. 8, 2016 for Application No. 10 162 186.0.
Product Datasheet "Phospholipid EFA"; MONA Industries [USA]; publication date unclear—possibly Nov. 1998.
"Water in Lip (Medicated La France Pear)" Shiseido [JP]; GNPD (Mintel); Nov. 2008.
"FirmA-Face XR Intant Temporary Invisible All Over Skin Tightener" Flageoli [USA]; GNPD (Mintel); Nov. 2009.
"Highlights Kit Extension" Clairol [USA]; GNPD (Mintel); Jul. 2005.
Product Datasheet "Lanette N"; Cognis Care Chemicals; May 2004.
Written submissions under Rule 116(1) EPC to the summons to attend oral proceedings on Apr. 28, 2016; EP Patent No. 2 371 220.
Analytical Report—Experimental Analysis of Clairol Product HI3F.
Examiner's Report Issued on Invention Patent Application;Chilean Patent Application No. 2742-2012, filed Sep. 28, 2012.
Response to Examiner's Report; Chilean Patent Application No. 2742-2012.
Office Action dated Oct. 6, 2016 received in Canadian Patent Application No. 2,793,135.
Response dated Apr. 6, 2017 to Office Action dated Oct. 6, 2016 received in Canadian Patent Application No. 2,793,135.
Office Action dated Jun. 5, 2017 received in Canadian Patent Application No. 2,793,135.
Office Action dated Mar. 30, 2016 received in Chilean Patent Application No. 2742-2012.
Response dated May 8, 2016 to Office Action dated Mar. 30, 2016 received in Chilean Patent Application No. 2741-2012.
Minutes of the Oral Proceedings before the Opposition Division received in EP Patent No. EP-B-2 371 220.
Interlocutory Decision in Opposition Proceedings received in EP Patent No. 2 371 220.
Amended Text of the Patent During Opposition Proceedings (Amended Drückexemplar) received in EP Patent No. 2 371 220.
Office Action from the Korean Intellectual Property Office dated Aug. 17, 2017 received in Korean Patent Application No. 10-2012-7028092.
Scientific Opinion of the Panel on Food Additives and Nutrient Sources added to Food; "Choline-stabilised orthosilicic acid added for nutritional purposes to food supplements"; The EFSA Journal; 2009; 948; pp. 1-23.

\* cited by examiner

STABILIZED BIO-AVAILABLE SOLUBLE SILICATE SOLUTION

CROSS REFERENCE TO RELATED APPLICATIONS

This application is a National Stage of International Application No. PCT/EP2011/054556, filed on Mar. 24, 2011, which claims priority from European Patent Application Nos. 10158686.5, filed on Mar. 31, 2010, and 10162186.0, filed on May 6, 2010, the contents of all of which are incorporated herein by reference in their entirety

TECHNICAL FIELD OF THE INVENTION

The present invention relates to the field of aqueous solutions comprising silicon in bio-available form. More particularly, the present invention relates to compositions of osmolyte stabilized alkali silicates suitable e.g. for use in plant fertilization programs or pharmaceutical, cosmetic or nutritional preparations, and to methods, such as e.g. for preparing osmolyte stabilized alkali silicates.

BACKGROUND

Silicon (Si) is not found in nature in its elemental (metal) form, although it is the second most abundant element after aluminum (Al) in the Earth's crust. Indeed, it has a very great attraction for oxygen and it forms a tetrahedral structure bound to four oxygen in its stable and most predominant form in water as monosilicic acid $Si(OH)_4$. This weak acid shows four acid functions with a lowest pKa value of 9.8. This implies that at pH 9.8 mono-silicic acid is present for 50% in the un-dissociated acid form and for 50% in the mono-ionic salt form (a silicate ion). The other pKa values are between 11.8 and 13.5. This means that only very strong alkali addition is able to dissociate all four acid groups into four silicate ions starting from silicic acid. At pH values higher than 10.8 silicates are predominantly formed.

Between pH 2 and 8 mono-silicic or ortho-silicic acid is a neutral molecule. It is predominantly uncharged between pH 2 and 3. At concentrations higher than 3 mM it starts to polymerize through a condensation reaction. It is therefore impossible without introduction of special stabilizing agents to synthesize high concentrations (≥4 mM) mono-silicic acid, stable in time at room temperature. During a first condensation reaction between two molecules mono-silicic acid and under liberation of a water molecule di-silicic acid is formed (i.e. the dimer $(OH)_3Si—O—Si(OH)_3$). This dimer is the crucial starting molecule for further polymerization reactions. Depending on the Si concentration, the temperature and the presence of other molecules or ions, polymerization proceeds with the formation of trimers, tetramers, and bigger oligomers (linear or cyclic). At higher concentrations bigger linear molecules silicic acid are formed which grow further and start to condense together forming colloidal structures or silica.

All these structures in suspension hydrolyze in time upon dilution and smaller molecules are again formed with consumption of water molecules.

Further polymerization of colloids results in the formation of amorphous silica under formation of precipitates or gel. Only the smallest forms of silicic acid (mono- and di-silicic) are bio-available for organisms (plants, algae, lichens, animals, human, etc.). These molecules are available in soil water, rivers, seas, sources, oceans, etc. The silicon concentration of these bio-available acids in water is limited to low concentrations (<3-5 mM). Especially plants and algae convert these acids into biogenic silica which is very slowly dissolved in water into mono-silicic acid.

During the last decade, evidence has come to exist that besides silicic acid also mono-silicates and mono-silicate complexes show bioavailability characteristics. Nevertheless, it is difficult to prove the bioavailability of these compounds.

Small silicic acid molecules are able to diffuse through all kind of cellular membranes and specific aquaporins (entry channels) or transporter proteins for mono-silicic acid were detected in plants and algae. It is evident that silicate ions (mono- or di-silicate ions) could enter membranes in a similar way. It is chemically difficult to show the difference between small silicic acids and their derived silicate ions. It is also possible that the silicate ions are converted into silicic acid during entry into the membrane or that they enter as a complex via another channel. Present invention starts from the finding that compatible solutes, which have their own specific aquaporins, are able to deliver silicates into the cellular membranes.

It is possible that silicic acid and silicates fulfill different activities in the cell. The cell specificity could be different for the ionic form in different organisms. We know that in plants, animals and human, both kinds of silicon are bioavailable and that structural or physiological effects are detectable after administration. Until now most accentuated effects were detected after supplementation of silicic acid.

Silicic acid is the natural bio-available silicon source in water. Silicon in food is present under different forms, mostly as biogenic silicic acid and complexes thereof with macromolecules as proteins and sugars. Silicate complexes and insoluble silicates may also be present. There is no correlation between the silicon content in food and the uptake of silicon in human. The bioavailability of the silicon compound is therefore important. The bioavailability of most compounds except for (mono) silicic acid is not studied.

It has been demonstrated, according to this invention, that supplementation of comparable amounts of osmolyte stabilized soluble silicates is able to show similar effects as silicic acid supplementation, whereas non stabilized silicates are less powerful.

The most common silicon forms in nature are silicic acid (from mono silicic acid to insoluble silica) and silicates. Most silicates are aluminosilicates present in soil minerals and rocks. These structures are stable and only broken down by physical forces (mechanical and biological fractures freeze thawing, etc.) followed by chemical weathering through activity of acids. Mono-silicic acid is formed as result from these chemical or biological reactions together with new silicates and is solubilized in water. Silicates form mainly very complex structures and may contain a mixture of different minerals. Silicates are normally solubilized and dissolved in strong alkaline conditions.

Most silicates are more soluble in water at high pH than silicic acid at pH between 2 and 8.

Silica (highly polymerized silicic acid) solubility in water is generally under 200 ppm. In highly concentrated silica industrial waters, silica is removed to inhibit membrane disturbing precipitation or deposition using reverse osmosis or on exchange techniques. Purified drinking water using these techniques contains therefore less or no silicon.

Silica particles exhibit irregular negative charges on the surface but they are not to be considered as real anions resulting in precipitation of salts. They truly precipitate as silicic acid and are only slowly solubilized. The more silica particles contain water (less cross-linking and more OH present) the easier they are solubilized again. The access of OH⁻ and water is essential for the dissolution of polymerized silicic acid and silicates into mono-silicic acid or mono-silicate.

Silica particles contain highly hydroxylated surfaces attracting and binding macro-molecules, containing OH groups, through hydrogen (O—H) bonds as polysaccharides, proteins, phenols, etc.

Silicates are industrially prepared from silica under strong alkaline conditions through dissociation of the Si—O—Si bond and ionization of the Si—OH acid group resulting in a Si—OM (M is a Metal ion) bond. The solubility of the resulting silicates depends on the concentration of OH ions supplemented and the degree of dissolution of Si—O—Si bonds. The higher the silica concentration the more alkaline is used for complete dissolution and solubilisation resulting in a higher mono- and di-silicate concentration, which is required for bioavailability.

The most interesting soluble silicates are the alkali metal silicates and preferably sodium and potassium silicates. They are synthesized from purified silica and highly soluble under alkaline conditions delivering especially mono- and di-silicates.

Such solutions contain normally a mixture of silicate anions. The building block of all these anions is the tetrahedral anion with a silicon atom in the center and oxygen in the corner of the four-sided pyramid: $SiO_4^{4-}$, similar to mono-silicic acid. This is the monomeric silicate anion (mono- or ortho-silicate anion). A hydrogen, potassium or sodium ion is associated with each oxygen. Upon polymerization, tetrahedra are linked with each other via Si—O—Si bonds. The negative charge of the unshared oxygen atoms is balanced by the presence of alkali cations, which are randomly spaced in the interstices of the silicate structure.

Because silicates are produced from silica different structures exist depending on the degree of silica polymerization, the concentration of added alkali hydroxide, and the degree of dissolution. Upon dissolution, solubilized silicates give rise to molecular speciation. The mixture of silicate anions in solution shows a complex of mono-, di-, tri- and higher linear, cyclic and three dimensional silicate anion structures represented by the general formulation $$xSiO_2:M_2O$$

where M is an alkali metal (lithium, sodium or potassium), with x representing the molar ratio (MR) of silica to metal oxide, defining the number of moles silica per mol alkali metal oxide. The higher the molar ratio, the less alkali metal ions are present in the silica network and the less alkaline the silicates are. For industrial applications, the weight ratio is indicated (WR) and is derived from the MR. For potassium silicate MR=1.56 WR. Potassium silicates are mostly produced with weight ratios ranging from 1.3 to 2.5.

In aqueous alkaline solution, a mixture of monomeric, oligomeric and polymeric silicate ions is formed which are in a dynamic equilibrium. This x ratio influences the distribution of anions. Lower (<2) ratios will result in higher concentration of mono and di-silicates and smaller oligomers while higher (>2.2) ratios will result in more complex structures, larger rings and polymers. The pH values of the concentrated products are usually between 10 and 13. Above pH 11-12 stable solutions of monomeric and polymeric silicate ions, without insoluble amorphous silica, are obtained but the solubility rapidly decreases when the pH is lowered to 9. Below this pH only a very small proportion is present as monomeric silicate anion besides insoluble silicate. Polymers or amorphous silica gels are formed, characterized by the loss of interstitial alkali ions from the three-dimensional network.

Dilution of concentrated silicate solutions in water results in new distributions of silicate structures. The pH of the diluted solution will drop and depending on the silicon concentration insoluble silicates are formed. The pH reduction of the diluted silicate is less than might be expected due to the buffering effect of the silicate and their pK values between 10 and 13. The silicates will slowly precipitate or polymerize.

The addition of acid at diluted samples is necessary to form silicic acid starting from concentrated silicate solutions (>0.1 M Si). The silicate anions are able to complex with OH containing macromolecules above pH 8. Soluble silicates can also react with multivalent cations, which are present in all kinds of water and media, forming the corresponding insoluble metal silicate resulting in a decreased bioavailability due to depletion of these ions.

Following soluble silicates are registered according to EU regulation
Sodium silicates ($NaO:xSiO_2$),
Disodium metasilicate, anhydrous,
Disodium metasilicate, pentahydrate,
Disodium metasilicate monohydrate,
Potassium silicates ($K_2O:xSiO_2$),
Lithium silicates ($Li_2O:XSiO_2$).

Silicon is not yet fully accepted as an essential element for all living organisms although there is ample evidence for beneficial effects in plants, microorganisms, animal and human.

The beneficial effects are particularly pronounced in plants exposed to abiotic and biotic stresses (Epstein E. (1999) Silicon Annual Review of Plant Physiology and Plant Molecular Biology, 50, 641-664). Epstein and Bloom even modified the definition of an essential element for plants to incorporate silicon (Epstein E. and Bloom A. J. (2005) Mineral Nutrition of Plants Principles and Perspectives; 2nd Edition Sunderland, M A, USA; Sinauer associates). In aboveground parts of the plant silicon concentration varies from 0.1 to 10.0% of dry weight. There are differences in silicon uptake and transport resulting in plant classifications regarding silicon uptake. There are plants showing an active uptake and silicon accumulation (some cyperaceous and graminaceous as rice, wheat, ryegrass and barley), other groups tolerate passive diffusion of silicon (some dicotyledonous as cucumber, melon, strawberry and soybean) while some dicots even exclude silicon (as tomato and bean). Silicon transporters were identified in rice responsible for root and xylem loading. There is little information for Si uptake and transport in the other monocots or dicots. It was shown that both active and passive mechanisms are operating in Si uptake and transport in Si accumulator plants (Epstein E. (2009) Annals of Applied Biology, 155, 155-160; Kvedaras O. L. et al. (2009) Annals of Applied Biology, 155, 177-186; Lang Y. C. et al. (2007) Environmental Pollution, 147, 422-428; Brunings A. M. et al. (2009) Annals of Applied Biology, 155, 161-170).

The authors of the present invention performed several experiments with silicon accumulator plants, silicon diffusion plants and silicon rejecting plants using a foliar spray application every week with strongly acidified silicates, resulting in a foliar application with guaranteed silicic acid (solution containing 0002 mg/ml Si).

In all these trials, there was a clear effect on the growth, production, resistance to infection, color of fruits; shelf life etc. showing that silicon is really taken up as silicic acid in all plants using foliar application. Some scientists reject the foliar application technique and only believe in the root amendment technique.

In general, in literature published experiments with silicon fertilization were conducted using either solid (ex.: calcium silicate and sodium silicate) mixed with the soil, or solubilized silicate solutions (ex.: sodium or potassium silicate) using a soil irrigation or a soil mixing technique with appropriate dilutions in process water (pH<9) containing multivalent minerals and other impurities. Silicon concentrations between 1 and 100 mM are normally used (1 mM Si=28 microgram Si/ml). Foliar application is not frequently used but similar concentrations are applied and this foliar application is believed to show less efficiency in laboratory experiments. During soil fertilization, silicates stay much longer around the roots and dissolve slowly while in the case of foliar applied silicates, the thin water-film containing silicon is quickly dried up.

Most authors claim that mono-silicic acid is the active ingredient instead of silicate. It is difficult or quite impossible to show that a diluted silicate concentrate is completely converted into silicic acid, the confirmed and proven bio-available compound. First, there is a drastic decrease in pH upon dilution generating polymerized silica. Omni present multivalent metal ions result in the formation of insoluble silicates and the lack of sufficient protons in process water pH>6 starting from concentrated Si solutions pH>12 inhibits the complete formation off silicic acid. Complexation with —OH containing natural compounds may also occur.

The present invention, using a mixture of selected osmolytes in highly concentrated soluble silicate solutions, resulted in a new formulation probably protecting the silicate ions from polymerization in their concentrated form and during dilution, showing high biological activity after dilution comparable to silicic acid.

Silicon confers tolerance in plants to various abiotic and biotic stresses. It does not only accumulate as biogenic silica through polymerization in cell walls inhibiting fungal or bacterial invasion, protects xylem fluidity, neutralizes toxic metals, acts against salinity and drought, affects structure, integrity and functions of membranes, inhibits lipid peroxidation, improves nutrient balance, increases shelf life of vegetables and fruits, etc.

During the last two decades there are hundreds of publications showing the benefits of silicon in plants, animals and human (Robberecht H. et al. (2009). Science of the Total Environment, 407, 16, 4777-4782; Sripanyakorn S. et al. (2009). British Journal of Nutrition, 102, 6, 825-834). Nevertheless, the suitable concentration, the speciation of the best and cheapest silicon compound, the optimal pH during application, the determination of the principal activity, and the synergies with other compounds is not yet proposed. There is even not a simple test to demonstrate biological activity in plants for a certain silicon composition.

In summary, Si is currently regarded as an essential nutritional element for plants, and there is ample evidence for beneficial effects in micro-organisms, animals and humans. Silicon is particularly beneficial for plants exposed to abiotic and biotic stresses. During the last decade, evidence has come to exist that, besides mono- and di-silicic acid, also silicates and silicate complexes could be sources of bio-available silicon to some extent.

The bottleneck in using silicic acids or silicates is their tendency to quickly precipitate and polymerise, thereby reducing their bio-availability. Silicates are only soluble in strong alkaline conditions. At pH<95 mono-silicic acid quickly polymerizes, resulting in the formation of trimers, tetramers, and bigger linear or cyclic oligomers. At higher concentrations bigger linear molecules of silicic acid are formed which grow further and start to condense into colloidal structures. Further polymerization of these colloids results in the formation of amorphous silica as precipitate or silica gel. Bioavailable silicon as silicic acid in water is only present at a concentration of <3-5 mM.

Soluble silicates are the alkali metal silicates such as sodium and so potassium silicates. They are synthesized from purified silica and highly soluble under alkaline conditions delivering especially mono- and di-silicates. Industrial preparation of silicates results in a concentrated silicate solution which needs to be diluted appropriately. However, these concentrated silicate solution are not very stable, neither are dilutions thereof. Upon dilution, the pH will drop and depending on the silicon concentration and the presence of multivalent metal ions, insoluble silicates are formed. Reaction with multivalent cations, e.g. from water or media, can cause the corresponding metal silicate to precipitate thereby reducing its bio-availability.

One approach for obtaining bio-available silicon is described in International patent application WO 2003/077657. Here, the use of silicic acid, such as orthosilicic acid, at very low pH and moderately alkalinized with basic compounds lacking free hydroxyl groups resulting in pH lower than 2 is described. No silicates are present in the preparation. This is a complete silicic acid approach.

One approach for obtaining bio-available silicon is described in International patent application WO 2001/047807. This patent describes the production of ortho-silicic acid through hydrolysis of a silicate into a solution of pH 0-4 in the presence of a non toxic solvent (liquid). Osmolytes are not mentioned nor needed for the production of the silicic acid solution. This is again a silicic acid approach.

There is thus a clear need in the art to produce bio-available silicon solutions from a cheap bulk material such as silicates, from which high concentrations can easily be obtained, with a high stability, both in concentrated as in diluted form. There is also a need to dilute the concentrated silicon solution with any type of water. Indeed, the stability of alkaline solubilised silicates upon dilution depends on the composition of the medium.

SUMMARY

It is an object of the present invention to provide good compositions for providing bio-available silicate to organisms and good methods for preparing bio-available silicate compositions.

The above objective is accomplished by a composition, method, and use according to the present invention.

The present invention relates to a stable aqueous silicate composition comprising alkali metal silicate, characterised in that the composition comprises at least a first osmolyte compound selected from urea and sugar alcohol and combinations thereof, and at least a second osmolyte compound selected from an N-methylated compound. It is essential that the alkali metal silicate is solubilised so as to be a source of bio-available silicon.

According to a preferred embodiment of the invention, the alkali metal silicate is selected from the group consisting of sodium silicate, potassium silicate, lithium silicate, and combinations thereof. It is an advantage of present invention that the dissolved silicate is an alkali metal silicate to achieve the stabilized dissolved state of the stable aqueous silicate composition of present invention.

It is an important feature of the present invention that the alkali metal silicate is stabilized within the stable aqueous silicate composition of present invention with minimally two osmolytes. As a result, the stable aqueous silicate composition is stable at room temperature for at least one year. Moreover, with the silicate being dissolved, the composition is a source of bio-available silicon for the health benefit of living organisms such as plants, micro-organisms, animal and humans.

Surprisingly, the stable aqueous silicate composition of present invention provides a source of bio-available silicon to plants, with the surprising effect that, when applied to crops, the rate of fungicides is reduced, the fungicidal efficiency of fungicides is enhanced, crop yield increases and the quality parameters of harvested crops improved.

It is an advantage of the present invention that the stable aqueous silicate composition is very versatile. It can thus be applied in, or added to, a whole range of products such as nutritional supplements, therapeutic compositions, cosmetic compositions, fertilizers, or plant protective compositions, and so on.

According to a preferred embodiment of the invention, the sugar alcohol is selected from the group consisting of glycerol, pinitol, galactitol, talitol, erythritol, threitol, arabitol, xylitol, ribitol, mannitol, sorbitol, dulcitol, iditol, maltitol, lactitol, polyglycitol, and combinations thereof. By preference, glycerol is used which is a cheap, widely available and easily applicable product.

According to another preferred embodiment of the invention, the N-methylated compound is selected from the group consisting of trimethylglycine, carnitine, N-methyl alanine, trimethylamino-butyric acid, proline-betaine, sarcosine, N-methyl-glycine, N,N-dimethylglycine, N-methyl aspartic acid, alanine-betaine, histidine-betaine, N-methyl taurine, choline, choline derivates, trimethyl-amine-N-oxide (TMAO), and combinations thereof and salts thereof.

The stable aqueous silicate composition can further, optionally, comprise a third osmolyte compound selected from the group consisting of taurine, creatine, choline-o-sulphate, glycerophosphorylcholine, diglycerol-phosphate, sulfonio-analogs of trimethylglycine, dimethylsulfoniopropionate, ectoine, hydroxyl-ectoine, proline, valine, aspartic acid, isoleucine, glycine, alanine, glutamate, sucrose, myo-inositol, fructose, maltose, trehalose, putrescine, spermidine, spermine, cadaverine, and combinations thereof and salts thereof.

The stable aqueous silicate composition can further, optionally, comprise one or more additives selected from the group consisting of a fertilizer, a plant protecting compound, a pesticide, a growth regulator, an adjuvant, a mineral, a biocide, a detergent, an emulsifier, a feed or food additive, a feed or food supplement, and combinations thereof. Advantageously, the composition of present invention is hence a composition with multiple health benefits to plants because not only does it provide bio-available silicon, it can also provide other protective or growth supporting compounds such as the fourth compound cited above.

Preferably, the concentration of multivalent metal ions within the stable aqueous concentrated silicate composition is lower than 10 mM and/or the pH of the composition is above 10.8 so as to support prolonged stability of the dissolved silicate.

Preferably also, the silicon concentration of the composition is from 0.02 to 1.60 M silicon.

Preferably, the first osmolyte compound is present at a concentration of at least 1.0% (w/v). The total osmolyte concentration of all osmolytes included in the composition is preferably lower than 70.0% (w/v).

In a preferred embodiment, the composition of the present invention is associated with one or more carriers, for example, e.g. absorbed on a non toxic carrier or on a gum, or adsorbed on a carrier such as a thickening agent or a bead.

The present invention also relates to a stable diluted aqueous silicate solution obtainable by diluting the stable aqueous silicate composition a according to the present invention at least 100 times, optionally at least 250 times, optionally at least 500 times, optionally at least 750 times, or optionally at least 1500 times.

It is an advantage of present invention that by using a mixture of selected osmolytes in highly concentrated soluble silicate solutions, such as the compositions of present invention, silicate ions are protected from polymerization, not only in their concentrated form but also after dilution, showing high biological activity even after dilution.

It is an advantage of present invention that the stable diluted aqueous silicate solution is suitable for conferring a health benefit to living organisms such as plants, micro-organisms, animal and humans.

Advantageously, the dilution can be carried out with any type of water available, such as drinking water, for example drinking water for animals. The dilution can also be mixed with food for human or animal consumption.

Preferably, the pH of the stable diluted aqueous silicate solution is from 5.0 to 10.0.

In a preferred embodiment, the stable diluted aqueous silicate solution of the present invention is associated with one or more carriers, for example, e.g. absorbed on a non toxic carrier or on a gum, or adsorbed on a carrier such as a thickening agent or a bead.

The present invention further relates to a powder obtainable by a process comprising the step of evaporating a stable aqueous silicate composition of present invention or a stable diluted aqueous silicate solution of present invention until a dry powder is obtained.

It is an advantage that this powder according to the present invention is easy to store, ship, market and handle. A powder is also a consumer friendly format as it is light in weight, easy to store until needed and it offers the benefit of resuscitating to the desired concentration in any type of water available.

The present invention also relates to the use of a stable aqueous silicate composition according to present invention or a stable diluted aqueous silicate solution according to present invention, for protecting crops or for preparing a pharmaceutical composition or a cosmetic composition or a food or feed supplement. As such, the stable aqueous silicate composition of the present invention can be used to provide bio-available silicon to living organisms.

The present invention also relates to a method for preparing a stable aqueous silicate composition.

The present invention furthermore relates to a method for protecting crops by applying to at least a portion of a surface of a crop an effective amount of the stable aqueous silicate composition of present invention.

The present invention furthermore relates to a kit of parts for contributing to the preparation of a stable aqueous silicate composition according to present invention or a stable diluted aqueous silicate solution according to present invention, the kit comprising at least an alkali metal silicate and at least a first osmolyte selected from urea and sugar alcohol and combinations thereof.

Optionally, the kit may also comprise a second osmolyte compound selected from an N-methylated compound.

Optionally, the kit may also comprise a third osmolyte compound selected from the group consisting of taurine, creatine, choline-o-sulphate, glycerophosphorylcholine, diglycerol-phosphate, sulfonio-analogs of trimethylglycine, dimethylsulfoniopropionate, ectoine, hydroxyl-ectoine, proline, valine, aspartic acid, isoleucine, glycine, alanine, glutamate, sucrose, myo-inositol, fructose, maltose, trehalose, putrescine, spermidine, spermine, cadaverine, and combinations thereof and salts thereof.

The present invention furthermore relates to a kit of parts for contributing to the preparation of a stable aqueous silicate composition according to present invention or a stable diluted aqueous silicate solution according to present invention, the kit comprising at least an alkali metal silicate; and at least a second osmolyte selected from an N-methylated compound.

Optionally, the kit may also comprise a first osmolyte selected from urea and sugar alcohol and combinations thereof.

Optionally, the kit may also comprise a third osmolyte compound selected from the group consisting of taurine, creatine, choline-o-sulphate, glycerophosphorylcholine, diglycerol-phosphate, sulfonio-analogs of trimethylglycine, dimethylsulfoniopropionate, ectoine, hydroxyl-ectoine, proline, valine, aspartic acid, isoleucine, glycine, alanine, glutamate, sucrose, myo-inositol, fructose, maltose, trehalose, putrescine, spermidine, spermine, cadaverine, and combinations thereof and salts thereof.

The present invention furthermore relates to an osmolyte compound solution for use as an ingredient for preparing a stable aqueous silicate composition according to present invention or a stable diluted aqueous silicate solution according to present invention, characterized in that the osmolyte compound solution comprises at least a first osmolyte compound selected from urea and sugar alcohol and combinations thereof.

Optionally, the osmolyte compound solution may also comprise a second osmolyte compound selected from an N-methylated compound.

Optionally, the osmolyte compound solution may also comprise a third osmolyte compound selected from the group consisting of taurine, creatine, choline-o-sulphate, glycerophosphorylcholine, diglycerol-phosphate, sulfonio-analogs of trimethylglycine, dimethylsulfoniopropionate, ectoine, hydroxyl-ectoine, proline, valine, aspartic acid, isoleucine, glycine, alanine, glutamate, sucrose, myo-inositol, fructose, maltose, trehalose, putrescine, spermidine, spermine, cadaverine, and combinations thereof and salts thereof.

The present invention furthermore relates osmolyte compound solution for use as an ingredient for preparing a stable aqueous silicate composition according to present invention or a stable diluted aqueous silicate solution according to present invention, characterized in the osmolyte compound solution comprises at least a second osmolyte compound selected from an N-methylated compound. Optionally, the osmolyte compound solution may also comprise a first osmolyte selected from urea and sugar alcohol and combinations thereof.

Optionally, the osmolyte compound solution may also comprise a third osmolyte compound selected from the group consisting of taurine, creatine, choline-o-sulphate, glycerophosphorylcholine, diglycerol-phosphate, sulfonio-analogs of trimethylglycine, dimethylsulfoniopropionate, ectoine, hydroxyl-ectoine, proline, valine, aspartic acid, isoleucine, glycine, alanine, glutamate, sucrose, myo-inositol, fructose, maltose, trehalose, putrescine, spermidine, spermine, cadaverine, and combinations thereof and salts thereof.

Particular and preferred aspects of the invention are set out in the accompanying independent and dependent claims.

Although there has been constant improvement, change and evolution of silicate compositions in this field, the present concepts are believed to represent substantial new and novel improvements, including departures from prior practices, resulting in the provision of more efficient, stable and reliable compositions of this nature.

The teachings of the present invention permit the design of improved methods and products for providing dissolved silicate. The above and other characteristics, features and advantages of the present invention will become apparent from the following detailed description, taken in conjunction with the accompanying figures, which illustrate, by way of example, the principles of the invention. This description is given for the sake of example only, without limiting the scope of the invention. The reference figures quoted below refer to the attached drawings.

Figure 1:
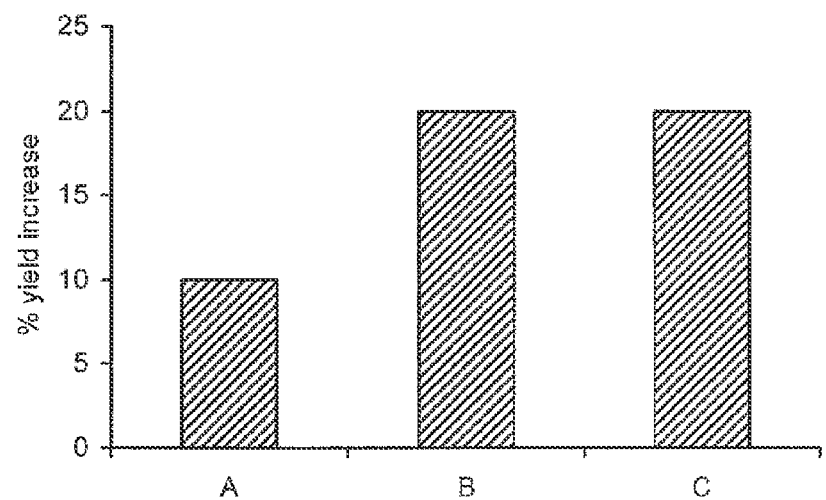
FIG. 1 is a graph showing the potato yield increase of *Alternaria solani* infected potato in three different field tests using varying levels of in fungicide 1 and/or a composition according to the present invention.

FIG. 3 is a graph showing the reduction of late blight infection of potato leafs in three different field tests without (empty bar) and with (striped bar) a composition according to the invention at 0.65 L/ha with various levels of fungicide.

FIG. 4 is a graph showing the potato yield increase of late blight infected potato in three different spraying programs of fungicides with a composition according to the invention at 0.65 L/ha.

FIG. 5 is a graph showing the effect on the quality of fruits harvested from field tests conducted in orchards without (empty bar) and with (striped bar) a composition according to the invention at 2 L/ha.

FIG. 6 is a graph showing the delay on storage disease contamination of fruits harvested from field tests conducted in orchards without (empty bar) and with (striped bar) a composition according to the invention at 2 L/ha.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings and figures described are only schematic and are non-limiting.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof.

The following terms are provided solely to aid in the understanding of the invention. These definitions should not be construed to have a scope less than understood by a person of ordinary skill in the art.

"Silicate" refers to silicates or silicate powders.

"Total osmolyte concentration" refers to the sum of the concentration of first, second and third osmolyte compound.

"Crops" can refer to any type of plant or product of a plant, such as fruits, vegetables, grains, legumes, trees, shrubs, flowers, grasses, roots, landscape plants, ornamental plants, and crop plants.

"Protecting crops" refers the ability of a product of the present invention to prevent and/or reduce and/or minimize undesirable effects of sun and/or heat. Undesirable effects of sun and/or heat on crops includes sunburn and heat stress, all of which may increase transpiration during photosynthesis, or cause visual damage to plant products such as fruits, vegetables, and fibres. Protecting crops also refers to the ability of a compound of the present invention to prevent and/or reduce and/or minimize insect infestation and/or damage to plant products.

As used in the present disclosure, the term "stability" specifically means that the individual silicates in the composition of the present invention refrain from polymerization (sol or gel formation), precipitation, coagulation or flocculation in suspension or coalescence on the bottom of the container. For practical purposes of the present disclosure, a suspension is considered to be stable if the polymerization or coagulation process is so slow as to take at least five days to form a perceptible precipitate in an undisturbed shipping container.

In a first aspect, the present invention relates to a stable aqueous silicate composition.

In a particular embodiment, this composition has a silicon concentration >0.02 M and a pH>10.8, and the molar concentration of the first osmolyte compound is higher than one fourth of the molar silicon concentration: [first osmolyte compound]>0.25 [Si].

In a second aspect, the present invention relates to a stable diluted aqueous silicate solution.

In a particular embodiment, the stable aqueous silicate composition of present invention is diluted so that a stable diluted aqueous silicate solution is obtained. Dilution can take place in all kinds of water or in a solution, an emulsion, a suspension, or in a drink, such as a soft drink, soup, coffee, tea, juice, or milk, or combinations thereof. As such, the stable diluted aqueous silicate solution is a source of bio-available silicon for pro- and eukaryotic cells, plants, animals and humans.

The pH of the stable diluted aqueous silicate solution is preferably between pH 5.0 and pH 10.0. For example, a 500 fold dilution of stable aqueous silicate composition of present invention containing 0.55 M Si could have a pH between 7.0 and 8.0, e.g. when diluted in tap water, or a pH between 8.0 and 9.0, e.g. when diluted in purified water.

In a particular embodiment, the composition or stable dilution thereof are associated with one or more carriers, e.g. absorbed on a non toxic carrier selected from the group consisting of cellulose, cellulose derivatives, proteins, salts, sugars, starch, modified starch, treated starch, starch phosphates and esters thereof, hydroxypropyl starch, and hydrolysed starch, and mixtures thereof resulting in a solution, emulsion, gel or suspension.

The stable aqueous silicate composition or stable dilution thereof are further particularly suited to be adsorbed on one or more carriers such as a thickening agent selected from the group consisting of gelatine, collagen, flour, fat, cereal grain, sugar, lactose, mannitol, polysaccharides, amino-sugars, sugar polymers, and gels, and mixtures thereof.

The stable aqueous silicate composition or stable dilution thereof are also particularly suited to be is adsorbed on one or more carriers such as a bead selected from the group consisting of alginate, alginate, cellulose, and pectin, and modifications and polymers and mixtures thereof.

In a particular embodiment, the composition or stable dilution thereof are absorbed on one or more carriers such as a gum selected from the group consisting of agar, alginic acid, beta glucan, carrageenan, dammar gum, glucomannan, guar gum, sodium alginate, and xantham gum, and mixtures thereof.

In a third aspect, the present invention relates to a powder.

In a particular embodiment, the stable aqueous silicate composition of present invention or a dilution thereof is evaporated so that a powder is obtained.

In a particular embodiment, the powder of present invention is associated with one or more carriers, e.g. absorbed on a non toxic carrier or on a gum, or adsorbed on a carrier such as a thickening agent or a bead.

In a fourth aspect, the present invention relates to the use.

As it can be understood from the above description, the stable aqueous silicate composition or stable dilutions thereof can be used in a wide range of applications as a source of bio-available silicon, for microbial, plant, animal and human applications.

In a particular embodiment the stable aqueous silicate composition or stable dilution thereof are used in the production of crops. Besides the dissolved silicate, the composition or stable dilutions thereof may further comprise plant protecting compounds, pesticides, growth regulators or other compounds used in crop production. More in particular, the composition can be used as a fertilizer such as a liquid fertilizer or plant protecting compound in foliar applications or drip irrigation. Thereto, it is mixed, for example, in an irrigation stream ("fertigation"), in soil fertigation or through liquid injection. It can for instance be used with a liquid spreader, spinning disc spreader, drop spreader, in furrow and flood irrigation, surface application and water run application.

In another particular embodiment the stable aqueous silicate composition or stable dilution thereof are used in a pharmaceutical composition or therapeutic formulation, or for preparing a pharmaceutical composition or therapeutic formulation such as in ointment, crème, milk, gel, water based liquid, emulsion, solution, lotion, mask, patch, spray, drink, beverage, syrup, capsule, pill, tablet, soft gel, etc.

In another particular embodiment the stable aqueous silicate composition or stable dilution thereof are used in a cosmetic composition or for preparing a cosmetic composition.

In another particular embodiment the stable aqueous silicate composition or stable dilution thereof are used in a food or feed supplement or for preparing a food or feed supplement.

In a fifth aspect, the present invention relates to an osmolyte compound solution for use as an ingredient for preparing a stable aqueous silicate composition according to present invention or a stable diluted aqueous silicate solution according to present invention, characterized in that the osmolyte compound solution comprises at least a first osmolyte compound selected from urea and sugar alcohol and combinations thereof. In a particular embodiment, the osmolyte compound solution could be, for example, an aqueous solution comprising urea, or sugar alcohol, or both, and optionally a second osmolyte compound selected from an N-methylated compound is present in or added to the latter osmolyte compound solution.

In a preferred embodiment, the osmolyte compound solution of present invention is for use as an ingredient for preparing a stable aqueous silicate composition according to present invention or a stable diluted aqueous silicate solution according to present invention, characterized in the osmolyte compound solution and comprises at least a second osmolyte compound selected from an N-methylated compound. In a particular embodiment, the osmolyte compound solution could be, for example, an aqueous solution comprising an N-methylated compound, and optionally a first osmolyte compound selected from urea and sugar alcohol and combinations thereof is present in or added to the latter osmolyte corn pound solution.

The N-methylated compound is, for example, an N-methylated compound selected from the group consisting of trimethylglycine, carnitine, N-methyl alanine, trimethyl-amino-butyric acid, proline-betaine, sarcosine, N-methyl-glycine, N,N-dimethylglycine, N-methyl aspartic acid, alanine-betaine, histidine-betaine, N-methyl taurine, choline, choline derivates and salts thereof, trimethyl-amine-N-oxide (TMAO), and combinations thereof and salts thereof.

In a sixth aspect, the present invention relates to a kit of parts for contributing to the preparation of a stable aqueous silicate composition according to present invention or a stable diluted aqueous silicate solution according to present invention, the kit comprising at least an alkali metal silicate and at least a first osmolyte selected from urea and sugar alcohol and combinations thereof.

Optionally, the kit may also comprise a second osmolyte compound selected from an N-methylated compound.

The present invention furthermore relates to a kit of parts for contributing to the preparation of a stable aqueous silicate composition according to present invention or a stable diluted aqueous silicate solution according to present invention, the kit comprising at least an alkali metal silicate, and at least a second osmolyte selected from an N-methylated compound.

Optionally, the kit may also comprise a first osmolyte selected from urea and sugar alcohol and combinations thereof.

The N-methylated compound is, for example, an N-methylated compound selected from the group consisting of trimethylglycine, carnitine, N-methyl alanine, trimethyl-amino-butyric acid, proline-betaine, sarcosine, N-methyl-glycine, N,N-dimethylglycine, N-methyl aspartic acid, alanine-betaine, histidine-betaine, N-methyl taurine, choline, choline derivates and salts thereof, trimethyl-amine-N-oxide (TMAO), and combinations thereof and salts thereof.

In a seventh aspect, the present invention relates to a method for preparing a stable aqueous silicate composition.

In a particular embodiment, the preparation of the stable aqueous silicate composition of present invention involves the stabilization with minimal two selected osmolytes. This preparation method involves, for example, the following steps.

First, an alkali silicate or silica powder is completely solubilized in a strong alkali hydroxide. Alternatively, solubilized alkali silicates may also be used. A concentrated silicon solution is thus obtained, with a silicon concentration higher than, for example, 3 M Si. Preferentially, the pH is increased with an alkali hydroxide until pH above 12.5. This strong alkaline silicate solution is subsequently diluted in a solution containing a sugar alcohol (e.g. glycerol), urea or a mixture of both. A clear solution is obtained. The second N-methylated osmolyte is then added. At this point, other optional osmolytes can be added. Preferably a silicon concentration between 0.02 and 1.6 M is obtained. The solution is kept at room temperature. Twenty fold or higher dilutions of this final preparation in mineral, purified or tap water result in a clear solution, stable for at least two weeks at room temperature.

In a particular embodiment, the method further comprises the step of adding an omit (alkali) soluble protein or protein hydrolysate from plant or animal origin at concentrations higher than 1% and preferably between 5% and 20%. The protein is added after dilution in purified water. Evaporation of the solution results in a powder containing bioavailable silicate.

In an eight aspect, the present invention relates to a method for protecting crops.

In a particular embodiment, crops are treated with a composition of present invention, such as a composition comprising dissolved silicate as a source of bio-available silicate as described above. More in particular, crops can also be treated with a composition of present invention comprising dissolved silicate as a source of bio-available silicate as well as one or more plant protecting compounds, pesticides, growth regulators or other compounds used in crop production. Crops are protected by providing the composition of the present invention in a required dose to a field of growing crops.

EXAMPLES

Example 1

Potassium silicate: 0.9 M Si
Glycerol: 10% (v/v)
UREA: 20% (w/v)
Trimethylglycine: 5% (w/v)
in water to make 100 vol. % (pH 13.0)

Example 2

Potassium silicate: 0.25 M Si
Glycerol: 25% (v/v)
UREA: 5%
Trimethylglycine: 3%
in water to make 100 vol. % (pH 12.3)

Example 3

Potassium silicate: 0.5 M Si
Glycerol: 25%
UREA: 20%
Potassium nitrate: 6%
Trimethylglycine: 3%
in water to make 100 vol. % (pH 12.9)

Example 4

Potassium silicate: 0.5 M Si
Glycerol: 20%
N-methyl-glycine: 6%
UREA: 20%
in water to make 100 vol. % (pH 12.8)

Example 5

Potassium silicate: 0.3 M Si
Glycerol: 20%
UREA: 20%

Sorbitol: 5%
Dimethylglycine: 5%
Potassium nitrate: 5%
in water to make 100 vol. % (pH 12.5)

Example 6

Sodium silicate: 0.3 M Si
Glycerol: 10%
Trimethylglycine: 3%
Mannitol: 10%
in water to make 100 vol. % (pH 12.4)

Example 7

Sodium silicate: 055 M Si
Glycerol: 15%
Trimethylglycine: 12%
Sucrose: 10%
in water to make 100 vol. % (pH 13.0)

Example 8

Potassium silicate: 055 M Si
Glycerol: 20%
TMAO (trimethyl-amine-N-oxide): 6%
Trimethylglycine: 6%
in water to make 100 vol. % (pH 12.8)

Example 9

Potassium silicate: 0.25 M Si
Trimethylglycine: 6%
L-proline: 10%
Glycerol: 10%
in water to make 100 vol. % (pH 12.5)

Example 10

Potassium silicate: 0.5 M Si
Trimethylglycine: 6%
Glycerol: 20%
Choline chloride: 20%
in water to make 100 vol. % (pH 12.9)

Example 11

Sodium silicate: 0.3 M
Glycerol: 25%
Trimethylglycine: 6%
Sorbitol: 8%
in water to make 100 vol. % (pH 12.3)

Example 12

Potassium silicate: 0.3M Si
Glycerol: 10%
UREA: 10%
Trimethylglycine: 1%
in water to make 100 vol. % (pH 12.9)

Example 13

Potassium silicate: 0.3M Si
Glycerol 15%
Urea: 10%
TMAO (trimethyl-amine-N-oxide): 1%
Lithium silicate: 0.02% Si
in water to make 100 vol. % (pH 12.9)

Example 14

Potassium silicate: 0.535 M Si
Glycerol: 20% (v/v)
Trimethylglycine: 5% (w/v)
Urea: 10% (w/v)
in water to make 100 vol. % (pH 12.9)

Example 15

Preparation of a Silicate Containing Composition without Compatible Solutes

We diluted potassium silicate (2.15 M Si, pH 13) 1000 times in purified water (pH 6.4), tap water (pH 6.6), mineral water (pH 7.0), process water (pH 6.5) used in green houses, liquid plant nutrient mixture and determined the final silicic acid (monomeric silicic acid or silicate) concentration, after stabilization at room temperature during 2 days, using the molybdenum blue method. $SiF_6$ was used as standard control for Si. Only the dilution in purified water resulted in acceptable values (more than 60% monosilicic acid or monosilicate detection). The other detection values were more than 50% lower. It is therefore obvious that the diluted silicates used in plant nutrition are in fact a mixture of solubilized mono-silicates, polymerized silicates and precipitated silicates in suspension.

Example 16

Water Holding Capacity of Crops Treated with a Control Silicic Acid Solution Lacking Osmolytes We developed a test after careful observation of plants treated with control solutions containing silicic acid and lacking osmolytes. Surprisingly we detected that plants treated (two times a week) with low doses (below 1 rail) of mono-silicic acid (solution 1) developed leafs that hold water much longer time than the control plants. The leafs were harvested (picked) and dried at room temperature or at 40° C. The interpretation of the results is straightforward and quick. Leafs from a three to six week old plant newly formed during silicon application were collected (picked off) and dried in open air after careful scattering on a plastic foil. Control (non silicic acid treated) leafs shrinked and dried much quicker than the silicon treated leafs.

To prepare the (control) silicic acid solution, a concentrated potassium silicate solution (pH 13.0) was first hydrolysed quickly in a strong acid pH smaller than 2.0 to obtain silicic acid (0.535 M Si). This concentrated solution was directly diluted in purified water resulting in a solution containing mono silicic acid and oligomers at much lower concentrations to inhibit polymerization in the absence of stabilizing osmolytes (solution 1). The same concentrated potassium silicate solution was diluted in process water pH 6.5 to a concentration of 0.7 mM Si as diluted silicate in process water without osmolytes. (solution 2)

Five week old white celery plants were treated (foliar spray) once a week during 5 weeks with the process water dilution (solution 2). Leafs from 3 plants were picked using scissors and dried at room temperature on a plastic foil. Already after 1-hour leafs started to curl while treated leafs conserved their original shape.

After 1 day, the difference was more accentuated. Control (non treated) and solution 2 treated plants shrinked, their colour became pale and dried up edges were visible while the solution 1 (silicic acid) treated plant still conserved their original shape and colour.

Example 17

Water Holding Capacity of Crops Treated with the Composition of Example 14

The composition of example 14 was diluted in tap water until a silicon concentration of 0.7 mM was reached, meaning a 750 fold dilution.

Four control preparations were made:

| | |
|---|---|
| Control 1 | a tap water dilution of a silicic acid ($H_4SiO_4$) solution containing 0.7 mM silicon as silicic acid of example 16 (silicic acid control) |
| Control 2 | a 750 fold tap water dilution of a solution of glycerol (20%), trimethylglycine (5%), and urea (10%) (Osmolyte control) |
| Control 3 | a 750 fold tap water dilution of a concentrated potassium silicate (0.535M silicon, pH 12.9), containing 0.7 mM silicon (silicate control) |
| Control 4 | tap water |

The experiment was performed with celery plants as described above. After 2 days of drying the celery leafs at room temperature on a plastic foil, two groups of leafs showed clearly superior water holding characteristics i.e. the control 1 group and the group that had been treated with the composition of example 14. The untreated group (control 4) showed completely shrinked leafs. Treatment with the control 2 and 3 preparations showed shrinked leafs similar to those of the untreated group (control 4), but the leaf edges were less dried out and the green colour was more preserved. There is an obvious similarity between the control 1 group and the group that had been treated with the composition of example 14. In these groups the morphology and shape of the celery leafs were practically not affected, their colour was best conserved and they were still flexible. This experiment shows that foliar application of silicic acid and diluted silicate prepared from concentrated alkali and stabilized with specific compatible solutes show similar biological effect on leafs. Silicic acid alone (control 1) does not need the osmolytes and the osmolytes alone (control 2) are not capable to induce the same effect. This experiment also shows that the addition of osmolytes to a silicate solution (i.e. the composition of example 14) is essential to confer plant protective properties as in the absence of osmolytes (i.e. control 3) no plant protective properties were observed.

This implies that application of osmolyte stabilized soluble silicates results in higher water retention and that therefore the plant is stimulated to produce specific structures to perform this crucial activity.

Example 18

Field Test Using a Dilution of Composition of Example 1 at Concentration of 0.375%

The composition of example 1 was applied to test the content of dry matter of vegetables. In this field test, a plot of celery received at 10 days interval 4 foliar sprayings of the composition of example 1 diluted in water at the rate of 0.375%, meaning a 266 fold dilution. At harvest, the yield and the volume of juice were measured (Table 1). The content of solid matter is calculated as the difference between the stem weight and the quantity of juice.

TABLE 1

Test results of treatment of a celery plot with the composition of example 1.

| Treatment | Stem weight (g) | Volume of juice (ml) | % Solid matter |
|---|---|---|---|
| Untreated | 650 | 550 | 16 |
| Treated | 950 (=+46%) | 450 | 47 |

The treatment with the composition did not only increase the stem weight, but also the content of solid matter. The increase of solid matter permits a longer shelf life of the freshly cut celery (further assessments have shown that the cut plants of celery treated with the composition of example 1 gained six days of freshness in comparison to non treated plants).

Example 19

A dilution in water of a composition containing:
Potassium silicate: 0.03 M Si
Collagen hydrolysate: 20% (w/v)
Trimethylglycine: 5% (w/v)
Xylitol: 8% (w/v)
This solution with pH 7.5 is quickly evaporated at a temperature lower than 70° C. into a powder.

Example 20

A dilution in water of a composition containing:
Potassium silicate: 0.01 M Si
Choline: 0.5% (w/v)
Mannitol: 2% (w/v)
Proline: 5% (w/v)
Carnitine: 2% (w/v)
Boric acid: 0.15% (w/v)
Citric acid: 0.1%
Sodium selenate: 0.01% (w/v)
This solution with pH 6.8 is diluted in drinking water for animal use.

Example 21

A dilution in water of a composition containing:
Potassium silicate: 180 mM Si
Trimethylglycine: 0.1% (w/v)
TMAO (trimethyl-amine-N-oxide): 0.9% (w/v)
Aspartic acid: 0.5% (w/v)
Urea: 0.2% (w/v)
Potassium nitrate: 2 (w/v)
A fungicide
This solution with pH 6.3 is used as fertilizer and osmolyte source for plants.

Example 22

One liter of the composition of example 9 is adsorbed on a mixture of 0.5 kg cellulose and 0.75 kg guar gum. The resultant paste is used as silicon and osmolyte source and mixed with animal food.

Example 23

Field Test Using the Composition of Example 12 to Treat *A. Solani* Infected Potato This composition was used for reducing the rate of fungicides.

The results are shown in FIG. 1 with (A): field test with ziram 76 WG at 1.5 kg/ha and no composition of example 12; (B): field test with ziram 76 WG at 1.5 kg/ha and composition of example 12 at 0.39 L/ha; (C): field test with ziram 76 WG at 2.5 kg/ha and no composition of example 12.

The addition of 0.5% of this composition of example 12, meaning a 250 fold dilution, equal to 0.39 L/ha, to a contact fungicide used at 60% of the authorised rate has permitted to achieve the same level of efficacy (1.5 kg/ha of fungicide instead of 2.5 kg/ha). Field test were conducted on Potato infected by *Alternaria solani*. Five treatments, spray volume of 260 L/ha.

Example 24

Field Test Using the Composition of Example 12 to Treat *E. Necator* Infected Grapes The composition of example 12 was used in a field test on grape infected by powdery mildew *Erysiphe necator*. Seven treatments, spray volume of 400 L/ha.

Figure 2:
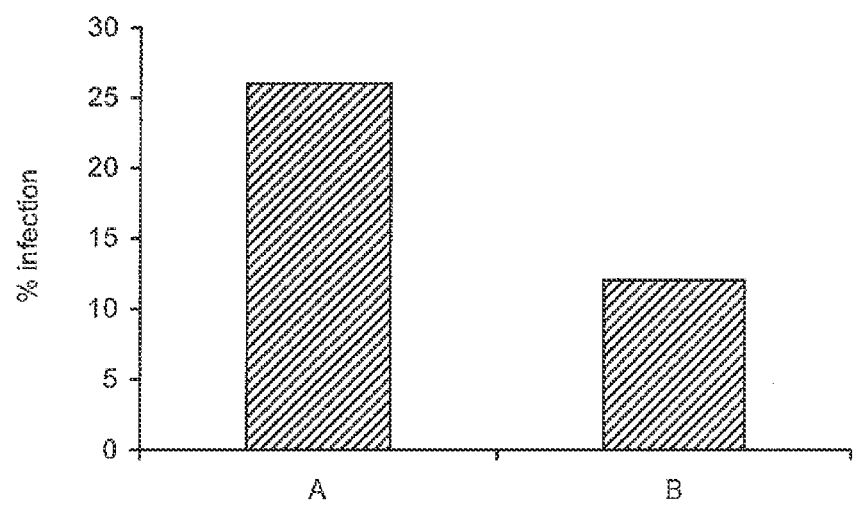
FIG. 2 is a graph showing the severity of powdery mildew infection of grapes: (A): untreated grapes; (B): grapes treated with a composition according to the invention at 1 L/ha.

The results are shown in FIG. 2. The composition of example 12 alone at 0.25%, meaning a 500 fold dilution, equal to 1 L/ha, has reduced the severity of the infection of powdery mildew by 54%.

Example 25

Field Test Using the Composition of Example 12 to Treat Late Blight Infected Potato The composition of example 12 was used in a field test performed on potato for the control of late blight (*Phytophtora infenstans*), three different types of fungicides (systemic, contact, curative) were applied alone and in combination with the composition of example 12 at the rate of 0.25%, meaning a 250 fold dilution.

Figure 3:
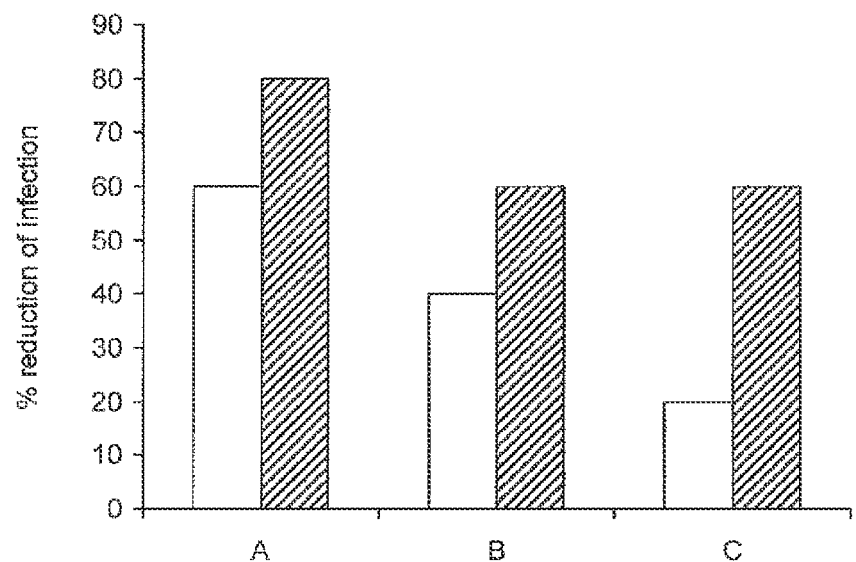

The results are shown in FIG. 3 with (A): field test with systemic fungicide 1 (propamocarb 72 SL) at 1.0 L/ha; (B): field test with contact fungicide 2 in (ziram 76 WG) at 3.0 kg/ha and composition of example 12 at 0.39 L/ha; (C): field test with contact fungicide 3 at 2.0 L/ha.

The addition of 0.25% of the composition of example 12, meaning a 500 fold dilution, equal to 0.65 L/ha, to the spray mix brought 60 to 200% more efficacy against Late Blight, whatsoever the type of fungicide In trial 1 fungicide 1 has a 60% efficiency, and fungicide 1+the composition of example 12 has a 80% efficiency. Accordingly, the composition of example 12 gives a 30% improvement of the efficacy of fungicide 1 in trial 1, a 50% improvement in of the efficacy of fungicide 2 in trial 2 and a 200% improvement in of the efficacy of fungicide 3 in trial Assessments were done on leafs after 8 treatments with a spray volume of 260 L/ha, with 50% of leafs infected in the non-treated leafs.

Example 26

Field Test Using the Composition of Example 12 on Potato

A 500 fold dilution of the composition of example 12 was used in a field test conducted on potato, assessing the increase of commercial yield due to eleven applications of the composition of example 12 at 0.65 L/ha. The impact of the composition of example 12 on yield has been evaluated with three different spraying programs of fungicides.

Figure 4:
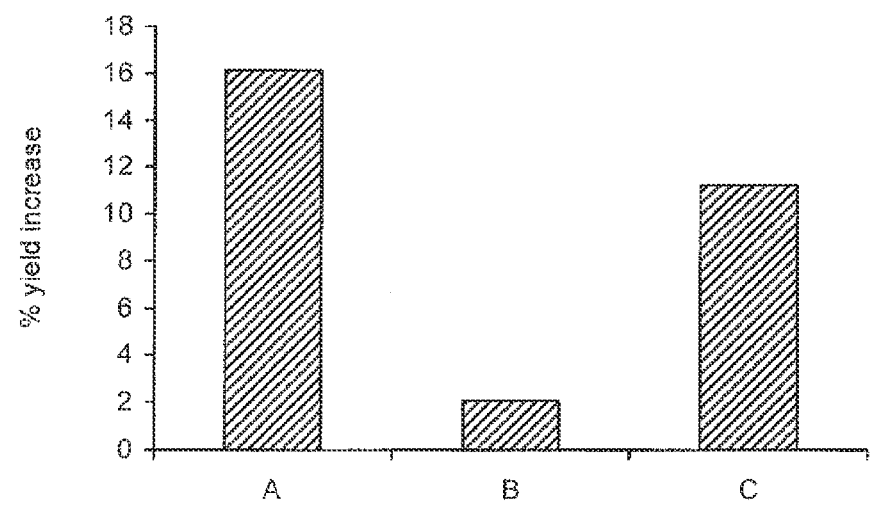

The results are shown in FIG. 4 with (A): spraying program with systemic fungicide 1 (propamocarbe 72 SL) at 1 L/ha; spraying program (B): spraying program with contact fungicide 2 (ziram 76 WG) at 3 kg/ha spraying program (C): spraying program with contact fungicide 3 at 2 L/ha. The commercial yield in the non-treated was 20.0 t/ha and the increase of yield due to the composition of example 12 ranged from 2.1 to 16.1%.

Example 27

Field Test Using the Composition of Example 12 on Plums (Mirabelle)

Figure 5:
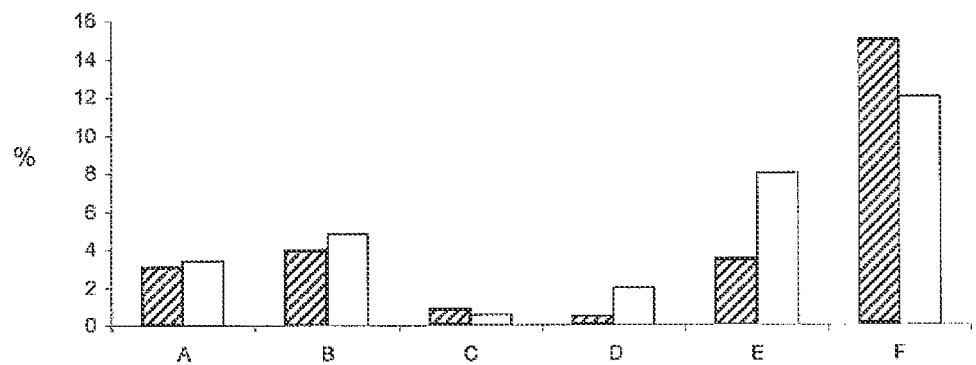

A 400 fold dilution of the composition of example 12 was used in a field test performed on plums (var. Mirabelle 1725) for assessing the effects of the composition of present invention on the quality parameters of the fruits produced, at harvest and during storage. Four applications of the composition of example 12 at the rate of 0.25% were done at weekly interval before harvest. The impact of the composition of example 12 was noticeable at harvest through assessment of acidity (FIG. 5, A), coloration (less green) (FIG. 5, B), pigmentation (FIG. 5, C), % of fruits contaminated by the disease Monilia (FIG. 5, D), % of over-mature fruits (FIG. 5, E) and fruits with peduncle (FIG. 5, F). All quality parameters of the fruits were improved by the invention in comparison to the non-treated.

Figure 6:
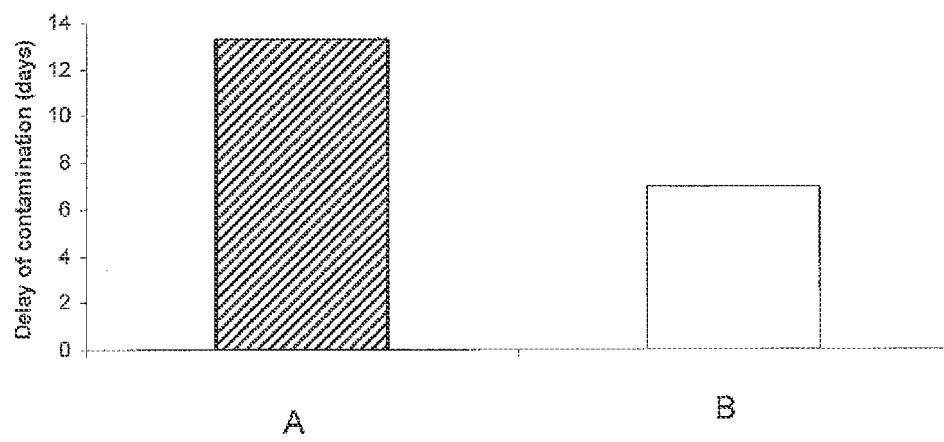

Fruits harvested from trees treated with the composition of example 12 were more resistant to the storage disease Monilia, allowing more than six additional days of storage in comparison to the control (FIG. 6).

It is to be understood that although preferred embodiments and specific concentrations and dilutions, as well as methods for preparing these, have been discussed herein for compositions according to the present invention, various changes or modifications in form and detail may be made. For example, whereas in the present invention for example a concentrated composition is described, the present invention also relates to any possible dilution of such concentrated composition.

The invention claimed is:

1. A stable aqueous silicate composition comprising a solubilized alkali metal silicate, characterized in that said composition further comprises
    at least a first osmolyte compound wherein said first osmolyte compound is a sugar alcohol selected from the group consisting of glycerol, pinitol, galactitol, talitol, erythritol, threitol, arabitol, xylitol, ribitol, mannitol, sorbitol, dulcitol, iditol, maltitol, lactitol, polyglycitol, and combinations thereof, and
    at least a second osmolyte compound selected from an N-methylated compound, wherein said N-methylated compound is selected from the group consisting of trimethylglycine, carnitine, N-methyl alanine, trimethylamino-butyric acid, proline-betaine, sarcosine, N,N-dimethylglycine, N-methyl aspartic acid, alanine-betaine, histidine-betaine, N-methyl taurine, choline, choline chloride, trimethyl-amine-N-oxide (TMAO), and combinations thereof and salts thereof, and
    wherein the pH of said composition is above 10.8.

2. The composition according to claim 1, wherein the sugar alcohol is glycerol.

3. The composition according to claim 1, further comprising one or more additives selected from the group consisting of a fertilizer, a plant protecting compound, a pesticide, a growth regulator, an adjuvant, a mineral, a biocide, a detergent, an emulsifier, a feed or food additive, a feed or food supplement, and combinations thereof.

4. The composition according to claim 1, wherein said composition comprises less than 10 mM multivalent metal ions.

5. The composition according to claim 1, wherein the silicon concentration is from 0.02 M to 1.6 M silicon.

6. The composition according to claim 1, wherein said first osmolyte compound is present at a concentration of at least 1% (w/v).

7. The composition according to claim 1, wherein the total osmolyte concentration is lower than 70% (w/v).

8. The composition according to claim 1, further comprising at least one carrier.

* * * * *